United States Patent
Gotou

(10) Patent No.: US 11,766,188 B2
(45) Date of Patent: Sep. 26, 2023

(54) MAGNETIC RESONANCE IMAGING DEVICE

(71) Applicant: HITACHI, LTD., Tokyo (JP)

(72) Inventor: Tomohiro Gotou, Tokyo (JP)

(73) Assignee: FUJIFILM HEALTHCARE CORPORATION, Chiba (JP)

( * ) Notice: Subject to any disclaimer, the term of this patent is extended or adjusted under 35 U.S.C. 154(b) by 354 days.

(21) Appl. No.: 16/636,389

(22) PCT Filed: Sep. 13, 2018

(86) PCT No.: PCT/JP2018/034002
§ 371 (c)(1),
(2) Date: Feb. 4, 2020

(87) PCT Pub. No.: WO2019/130675
PCT Pub. Date: Jul. 4, 2019

(65) Prior Publication Data
US 2020/0170537 A1 Jun. 4, 2020

(30) Foreign Application Priority Data
Dec. 26, 2017 (JP) ................................ 2017-248769

(51) Int. Cl.
*A61B 5/055* (2006.01)
*G01R 33/565* (2006.01)
*G01R 33/567* (2006.01)

(52) U.S. Cl.
CPC .......... *A61B 5/055* (2013.01); *G01R 33/5676* (2013.01); *G01R 33/56509* (2013.01)

(58) Field of Classification Search
CPC .............. A61B 5/055; G01R 33/56509; G01R 33/5676
See application file for complete search history.

(56) References Cited

U.S. PATENT DOCUMENTS 9,671,482 B2 *   6/2017  Oh ......................... A61B 5/721
2007/0120565 A1 *  5/2007  Iwadate ............. G01R 33/5676
                                                324/318
(Continued)

FOREIGN PATENT DOCUMENTS

JP  2006-026076 A  2/2006
JP  2007-185300 A  7/2007
(Continued)

OTHER PUBLICATIONS

Notice of Reasons for Refusal, dated Oct. 12, 2021, for Japanese Patent Application No. 2017-248769 (with English translation).
(Continued)

*Primary Examiner* — Christopher Koharski
*Assistant Examiner* — Sean A Frith
(74) *Attorney, Agent, or Firm* — Baker Botts L.L.P.

(57) ABSTRACT

To suppress the image quality deterioration due to respiratory motion and changes thereof, and improve the data acquisition rate. An MRI device according to the present invention repeats a main measurement in a predetermined unit, and performs a navigation measurement to acquire one or a plurality of the navigator echoes between the measurements in the temporally adjacent two predetermined units, and performs determination as to whether to continue or discontinue the main measurement and determination as to whether to discard immediately prior measurement data. In the determination, at least two navigator echoes are used, and by using a position of a site to be monitored by the navigation measurement and a displacement width serving as a reference of the displacement stability, whether the position and the displacement width satisfy a reference displacement and a reference displacement width, which have been obtained in advance, is determined.

9 Claims, 13 Drawing Sheets

(56) References Cited

U.S. PATENT DOCUMENTS

2013/0281823 A1* 10/2013 Stemmer .............. A61B 5/7207
  600/410
2014/0210469 A1* 7/2014 Cheng .............. G01R 33/56509
  324/309
2017/0205487 A1* 7/2017 Zeller ................ G01R 33/4835

FOREIGN PATENT DOCUMENTS

| JP | 2012-000306 A | | 1/2012 | |
|----|---------------|---|--------|---|
| JP | 2012000306 A | * | 1/2012 | |
| JP | 2013-230386 A | | 11/2013 | |
| JP | 2015-002834 A | | 1/2015 | |
| WO | WO 2004/080301 A | | 9/2004 | |
| WO | WO-2004080301 A1 | * | 9/2004 | ......... G01R 33/5676 |

OTHER PUBLICATIONS

International Search Report, dated Nov. 12, 2018, which issued during the prosecution of International Application No. PCT/JP2018/034002, which corresponds to the present application.

International Preliminary Report on Patentability including Written Opinion of the International Searching Authority, dated Jun. 30, 2020, for International Application No. PCT/JP2018/034002.

* cited by examiner

MAGNETIC RESONANCE IMAGING DEVICE

TECHNICAL FIELD

The present invention relates a magnetic resonance imaging (MRI) device that measures a nuclear magnetic resonance signal from hydrogen, phosphorus, and the like in a subject, and images the density distribution, the relaxation time distribution, and the like of the nuclear, and specially relates to a technique of acquiring a navigator signal that detects body motion of the subject, and controlling imaging.

BACKGROUND ART

In the imaging using an MRI device, a nuclear magnetic resonance signal (echo) generated from a tissue of a subject excited by a high frequency magnetic field of a nuclear magnetic resonance frequency is measured and imaged. In this case, by applying gradient magnetic field pulses in a plurality of directions orthogonal to each other, position information is given to the nuclear magnetic resonance signal. Occurrence of body motion such as respiratory motion of the subject during the imaging shifts a position of the gradient magnetic field, which causes the degradation of the image or a position shift of a result image.

To cope with this problem, known have been a method in which respiratory motion is monitored by a pressure sensor or the like, and imaging is performed in synchronization with a respiratory cycle (respiratory synchronization measurement), and a method in which a nuclear magnetic resonance signal, which is called a navigator echo, separately from an echo for acquiring an image, is acquired from a site with a large respiratory motion displacement, for example, a diaphragm or an abdominal wall, respiratory motion displacement is detected by the navigator echo, respiratory gating is performed, and the acquired image is corrected (for example, Patent Literature 1, Patent Literature 2, and the like). The navigator echo method has such an advantage that a sensor for detecting body motion is unnecessary, and body motion in an arbitrary site can be monitored.

CITATION LIST

Patent Literature
Patent Literature 1: JP-A-2007-185300
Patent Literature 2: JP-A-2015-2834

SUMMARY OF INVENTION

Technical Problem

In the respiratory synchronization measurement, the measurement for imaging is performed during a period in which the respiratory motion is stable based on the monitored body motion position, which results in a low acquisition efficiency of data, and easy occurrence of the image quality deterioration due to change in a respiratory state of the subject. In the navigator echo method, although the image quality deterioration due to the change in the respiratory state can be suppressed, data is acquired at the time point when the respiratory motion displacement enters a gate window that corresponds to a stable period of the respiratory motion set in advance, so that the low data acquisition rate has been unsolved.

The present invention addresses the problem of providing a technique that suppresses the image quality deterioration due to body motion, specially respiratory motion and changes thereof, and improves the data acquisition rate.

Solution to Problem

In order to solve the abovementioned problems, an MRI device according to the present invention performs a measurement that acquires image data a plurality of divided times, performs acquisition of an extremely short navigator echo during the divided measurements, and determines whether the acquisition of image data can be continued.

In other words, an MRI device according to the present invention is provided with: a measurement section that executes a navigation measurement to acquire a navigator echo that specifies a cyclic displacement of an object to be inspected, and a main measurement to acquire an image of the object to be inspected; and a control section that controls an operation of the measurement section such that after having performed the navigation measurement over at least one cycle of the cyclic displacement, the measurement section repeats the main measurement in a predetermined unit, and performs the navigation measurement to acquire one or a plurality of the navigator echoes between the measurements in the temporally adjacent two predetermined units. The control section includes a determination section that determines, by using the navigator echo acquired over the one cycle of the cyclic displacement in the navigation measurement, a reference position and a reference displacement width in the cyclic displacement, and determines, by using a navigator echo acquired immediately after the measurement in the predetermined unit, and the reference position and the reference displacement width, whether to continue or discontinue the measurement in the predetermined unit, and the measurement section repeats the measurement in the predetermined unit when the determination section has determined to continue the measurement in the predetermined unit, and performs the navigation measurement when the determination section has determined to discontinue the measurement in the predetermined unit.

Advantageous Effects of Invention

With the present invention, when the main measurement is repeated in the predetermined unit, a navigator echo is measured between the measurements in the predetermined units, and determines, based on a displacement obtained from the acquired navigator echo and the reference position/reference displacement width determined before the main measurement, whether the measurement in the predetermined unit is further continued, so that it is possible to correspond to the change in the respiratory state, and secure the utmost measurement without a loss time.

DESCRIPTION OF EMBODIMENTS

Figure 1:
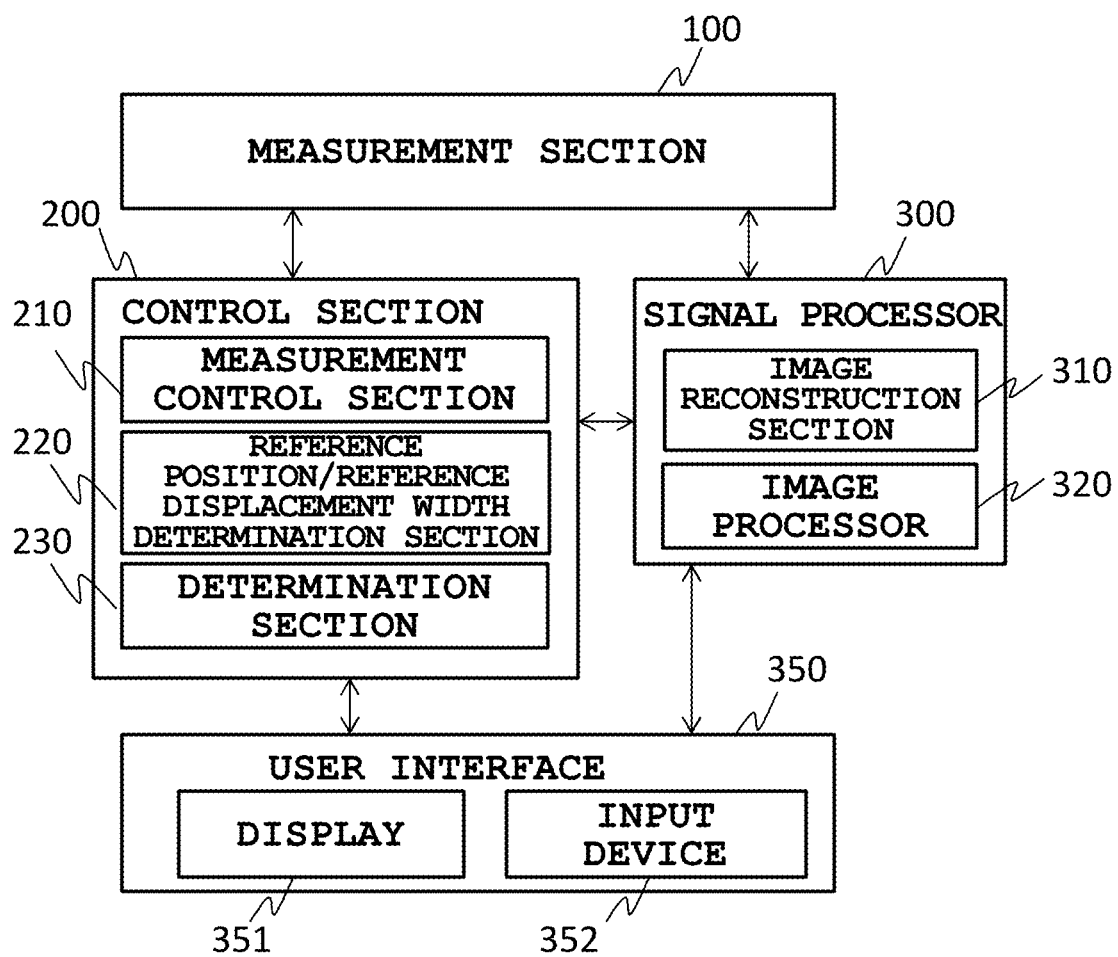
FIG. 1 is a functional block diagram illustrating an embodiment of an MRI device according to the present invention.

One embodiment of an MRI device according to the present invention will be described with reference to FIG. 1. As illustrated, the MRI device in the present embodiment is provided with a measurement section 100 that measures a nuclear magnetic resonance (MR) signal, a control section 200 that controls an operation of the measurement section 100, and a signal processor 300 that performs computation such as an image reconstruction using the MR signal measured by the measurement section 100. The MRI device can further be provided with a user interface (interface section) 350 with input and output devices (a display 351 and an input device 352) with which a user inputs an instruction or data and the like necessary for processing into the control section 200 and the signal processor 300, and displays a result of the processing.

Figure 2:
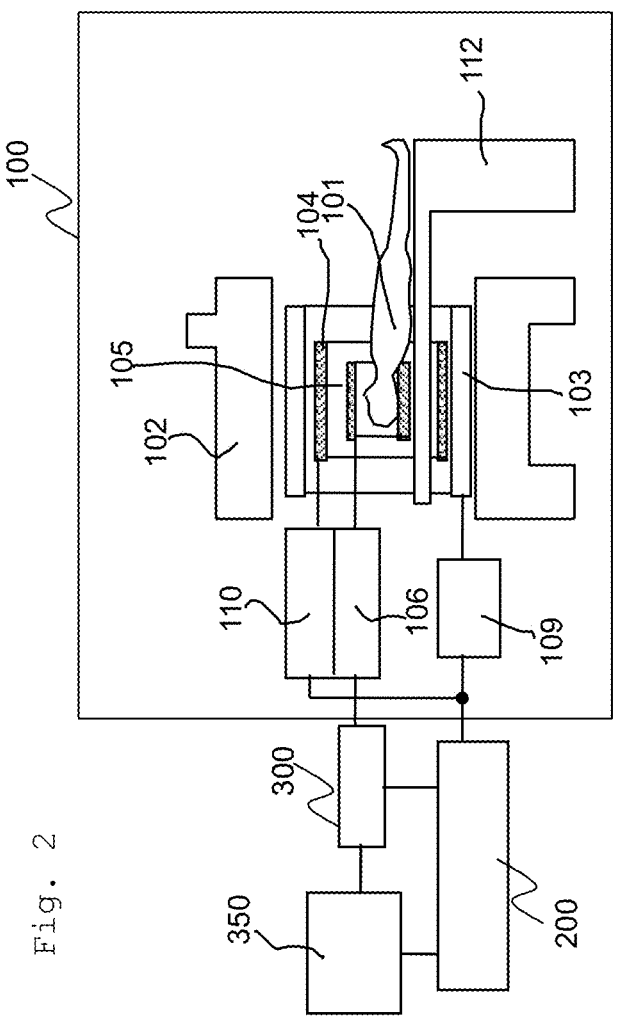
FIG. 2 is a diagram mainly illustrating a configuration of a measurement section of the MRI device in FIG. 1.

The configuration of the measurement section 100 is similar to that of general MRI devices, and is provided with, for example, as illustrated in FIG. 2, a magnet 102 that generates a static magnetic field in the surrounding of a subject 101, a gradient magnetic field coil 103 that generates a gradient magnetic field in a gradient magnetic field space to be generated by the magnet 102, a high frequency coil (RF coil) 104 that generates a high frequency magnetic field in a prescribed region of the subject, and a RF probe 105 that detects an MR signal to be emitted by the subject 101. The gradient magnetic field coil 103 includes gradient magnetic field coils in three directions of X, Y, and Z, which respectively generate gradient magnetic fields in accordance with signals from a gradient magnetic field power supply 109. The RF coil generates the high frequency magnetic field 104 in accordance with a signal from an RF transmitter 110. The signal from the RF probe 105 is detected by a signal detector 106, and is transferred to the signal processor 300.

The signal processor 300 is provided with an image reconstruction section 310 that subjects an MR signal to Fourier transformation to create image data, an image processor 320 that performs correction processing, image-to-image computation, and the like relative to the MR signal and the created image, and other sections.

The control section 200 controls operations of the measurement section 100 and the signal processor 300. The control of the measurement section 100 is performed, in accordance with a pulse sequence in which the intensity and application timing of the high frequency magnetic field pulse and the gradient magnetic field pulse, the reception time (A/D time) of the MR signal, and the like are defined, to control the drive of the gradient magnetic field power supply 109, the RF transmitter 110, and the signal detector 106. The pulse sequences of different types depending on objects and methods of the imaging are programed in advance and stored in a memory or the like, and are selected and executed in accordance with an inspection protocol or designated by a user with an imaging condition.

The MRI device in the present embodiment executes a sequence to measure a navigator echo (navigation measurement), and a pulse sequence of a measurement (main measurement) for acquiring an image of the subject 101. In that case, the control section 200 controls whether to continue or discontinue the main measurement, by using a displacement in a predetermined site of the subject 101 that is calculated from the measured navigator echo. Therefore, the control section 200 is provided with, as illustrated in FIG. 1, function sections such as a measurement control section 210, a reference position/reference displacement width determination section 220, and a determination section 230.

The control section 200 can include a CPU and a memory, and can implement apart or all of the abovementioned functions by a program mounted on the CPU. It should be noted that a part of the functions can be substituted by hardware such as an application specific integrated circuit (ASIC) and a field programable gate array (FPGA). Moreover, a part of the functions (for example, the image reconstruction and the correction calculation) of the signal processor 300 can be implemented by the same CPU as that of the control section 200.

Next, imaging by the MRI device in the present embodiment will be described using a case where the cyclic displacement is respiratory motion as an example.

Figure 3:
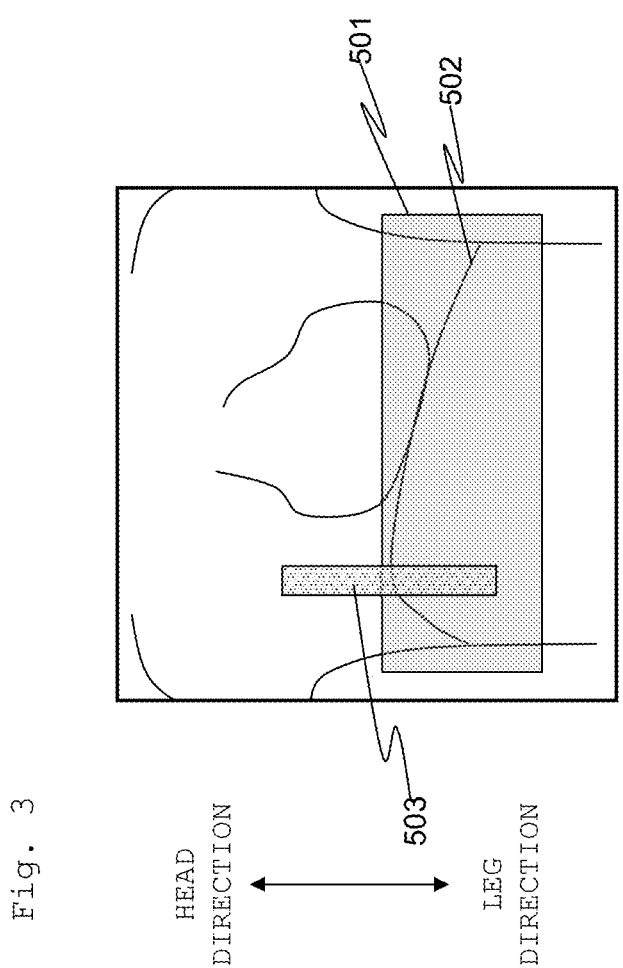
FIG. 3 is a diagram illustrating a site to be imaged in a main measurement, and a site to which a navigation measurement is executed.

FIG. 3 is a diagram illustrating a chest of a subject, and a region surrounded by solid line as a rectangle is a region (slab) 501 serving as an object to be imaged. In this example, a navigation measurement region 503 is set so as to include a diaphragm 502 along a body axis direction of the subject. The user can set the imaging region 501 and the navigation measurement region 503, for example, on an image (scout image) of the subject in a wide region imaged at a low resolution imaging, with the user interface 350.

The pulse sequence to be used in the imaging is not specially limited, but repeats, in order to acquire echo signals necessary for the image reconstruction from the imaging region 501 having a prescribed width, a step of collecting one or a plurality of echo signals. In the navigation measurement, by using a two-dimensional excitation RF pulse or in combination with the RF pulse and gradient magnetic field pulses in a plurality of directions, a desired pillar region (navigation measurement region) is excited, and an echo signal (navigator echo) is measured from the navigation measurement region 503. A profile can be obtained by subjecting the navigator echo to one-dimensional Fourier transformation in the image reconstruction section 310, and an anatomically characteristic position that is present in the pillar region, for example, a position of a diaphragm, can be detected.

Figure 4:
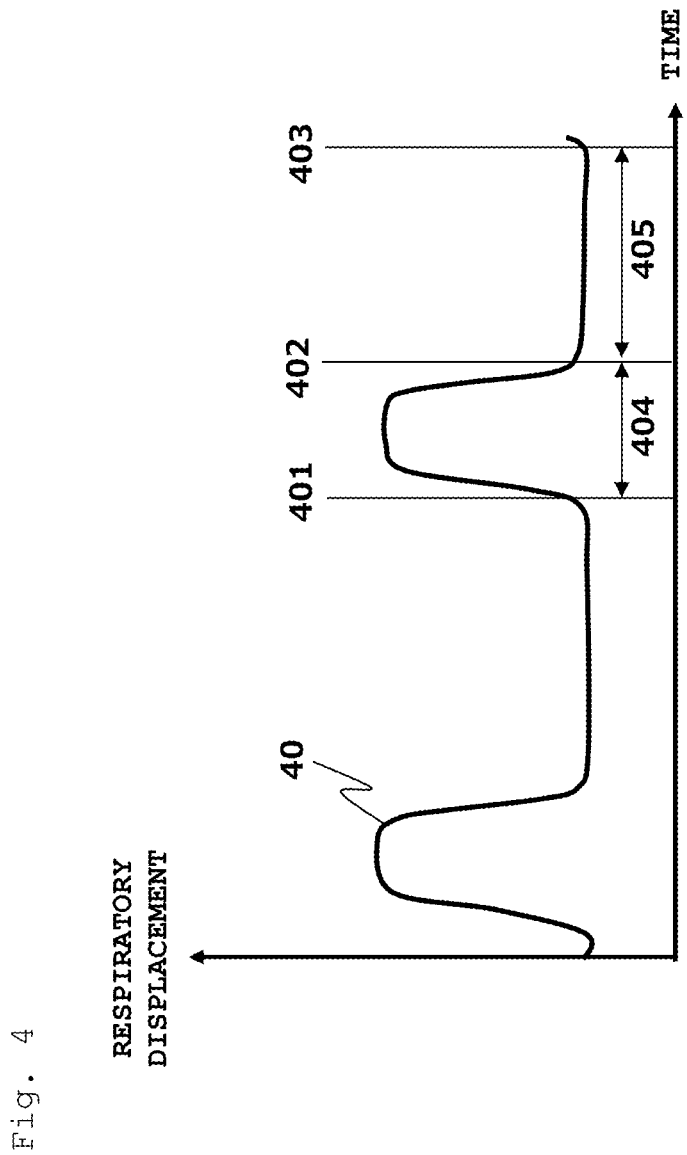
FIG. 4 is a diagram illustrating a respiratory displacement.

In the displacement of the diaphragm, as illustrated in FIG. 4, a duration 405 in which the displacement is comparatively stable is present in an inspiration cycle of the cyclic respiratory motion. In the imaging in the present embodiment, imaging (main measurement) for acquiring image data is performed by making the utmost use of the duration in which the displacement is stable. At the time other than the imaging, the navigation measurement is performed, and it is detected that the displacement has deviated from the stable duration 405 and that the displacement has entered the stable duration 405. For that, the main measurement is repeated in a predetermined unit, the navigation measurement to acquire at least one navigator echo during one measurement is performed, and continuous monitoring of the displacement is performed.

Hereinafter, a specific example of measurement control by the measurement control section 210 will be described.

First Embodiment

In the present embodiment, the reference position/reference displacement width determination section 220 determines, by using a navigator echo acquired over one cycle of a respiratory displacement in the navigation measurement, a reference position and a reference displacement width in the respiratory displacement, and the determination section 230 determines, by using a navigator echo acquired immediately after the main measurement in a predetermined unit, and the reference position and the reference displacement width, whether to continue or discontinue the measurement in the predetermined unit. Moreover, the measurement section 100 repeats the measurement in the predetermined unit when the determination section 230 has determined to continue the measurement in the predetermined unit, whereas performs the navigation measurement and discards the data acquired in the immediately prior measurement in the predetermined unit when the determination section has determined to discontinue the measurement in the predetermined unit.

Hereinafter, an operation of the MRI device in the present embodiment will be described with reference to the flow in FIG. 5.

When imaging is started, the measurement control section 210 controls the measurement section 100 so as to perform a navigation measurement, and acquires a navigator echo (S101). The navigation measurement is performed during a period of at least one cycle or more of the respiratory motion of the subject, a displacement (change in a position) in a specific site of the subject is detected from the acquired navigator echo during the period, a section in which the change in a position is within a displacement width determined in advance and a duration thereof is the longest is obtained, and the displacement in the specific site in the section is set as a reference displacement. Further, a width of the reference displacement, in other words, a displacement width determined in advance is set as a reference displacement width, and a prescribed position in the reference displacement is set as a reference position (S102). As the prescribed position, a mean value, a maximum value, a minimum value of positions in the reference displacement, or the like can be employed. The reference position and the reference displacement width are used as a reference that is used by the determination section 230 to determine whether to start or continue the main measurement, and to determine whether to store data in the immediately prior measurement.

In addition, the measurement section 100 executes the navigation measurement (S103), and starts, if a position of a specific site (for example, diaphragm) specified from the navigator echo satisfies the reference (S104), the main measurement (S105). If the position does not reach the reference displacement, the navigation measurement at S103 is continued.

The main measurement collects, for example, entire data necessary for reconstructing one or a plurality of images in a plurality of divided times. In other words, part of data among the entire data is collected in one measurement, and the measurement is repeated to collect the entire data.

In the main measurement being repeated, the navigation measurement (S106) is performed between one measurement and the next measurement, and the navigator echo acquired in that process is compared with a navigator echo acquired immediately prior to the main measurement (S105) to determine whether a position (detect position) detected from the acquired navigator echo is within the reference displacement and whether the width of displacement to be obtained from two or more navigator echoes is within the reference displacement width (S107).

At a determination step S108, if the detected position is not the reference displacement or the displacement width exceeds the reference displacement width, data in the immediately prior main measurement is discarded (S108, S109), and the navigation measurement (S106) is repeated until the determination condition becomes "YES".

At the determination step S108, if it has been determined that the position detected in the navigation measurement (S106) is within the reference displacement and a displacement width to be obtained from adjacent two or more navigator echoes is within the reference displacement width, a counter of the number of repetitions of the pulse sequence is incremented, and the next measurement is performed (S105).

The main measurement divided into predetermined units and the navigation measurement are alternately executed in this manner, and if it has been determined after the navigation measurement (S106) that the displacement of the subject and displacement width do not satisfy the references, the next main measurement is stopped, and only the navigation measurement (S106) is executed until the reference is satisfied. Eventually, the imaging is ended at a time point when the scheduled number of repetitions of the measurement has been ended (S110).

Next, a specific content of the abovementioned processing will be described.

[Determination of Reference Position/Reference Displacement width: S101, S102]

Figure 5:
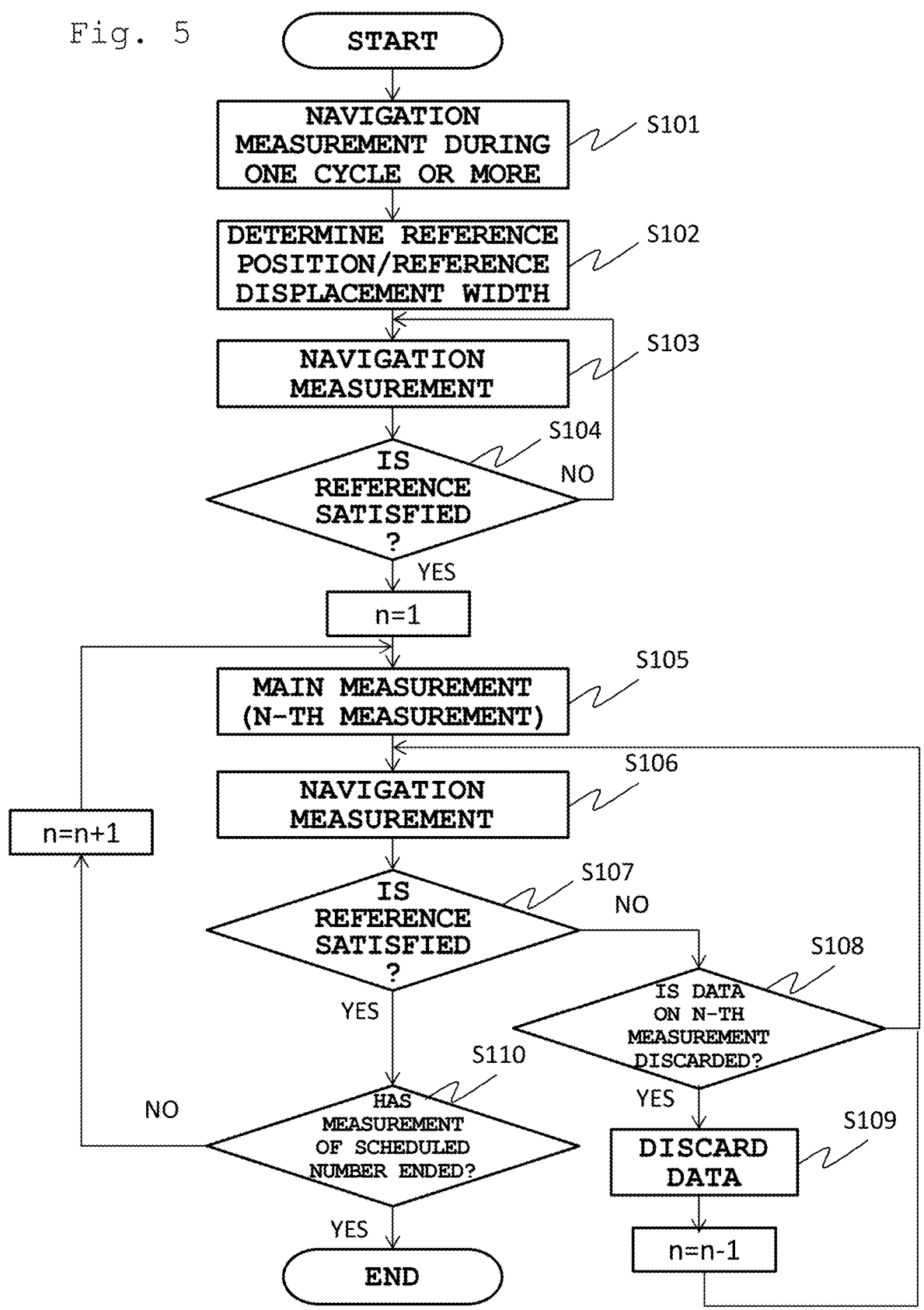
FIG. 5 is a flowchart illustrating an imaging procedure by an MRI device in a first embodiment.
Figure 6:
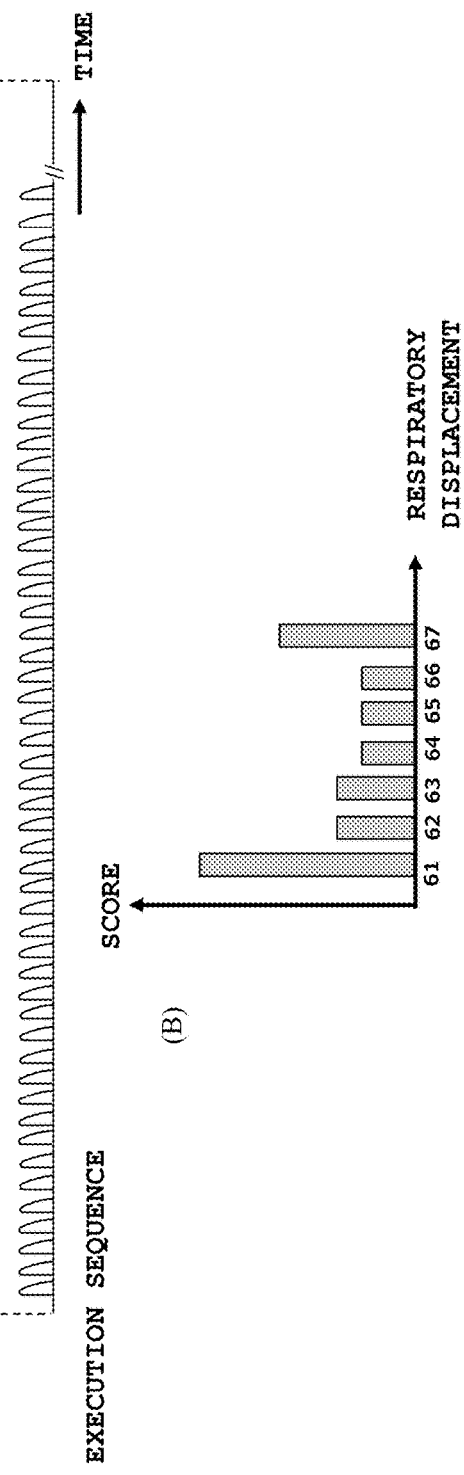
FIG. 6 is drawing for explaining the determination of a reference position in a cyclic displacement, FIG. 6 (A) is a diagram illustrating the respiratory motion and regions of displacement, and FIG. 6 (B) is a histogram illustrating a navigator echo score for each region.

Firstly, at the steps S101 and S102 illustrated in FIG. 5, the navigation measurement is continuously executed during at least one cycle, and the reference position/reference displacement width determination section 220 thereafter determines a reference displacement and a reference displacement width serving as references to determine a displacement and a displacement width. An example of a determination method of a reference displacement and a reference displacement width will be described with reference to FIG. 6. FIG. 6 (A) illustrates a displacement (respiratory displacement) of a cyclic movement detected by the navigator echo, and illustrates timing of the navigation measurement below. The horizontal axis represents time. In one navigation measurement, a region (FIG. 3: the navigation measurement region 503) including a diaphragm is excited, a navigator echo occurred from the region is acquired, and the echo signal is subjected to Fourier transformation, thereby obtaining position information on the diaphragm. One navigator echo may be acquired from one navigation measurement.

In order to obtain a period in which the respiratory displacement is stable, which is suitable for the main measurement, as illustrated in FIG. 6 (A), the cyclic movement is divided into a plurality of displacement regions (of level) 61 to 67, and the score of the navigator echo measured during one cycle is counted for each region. For example, as illustrated in FIG. 6 (B), the score of the navigator echo for each region becomes large in a region corresponding to the period in which the respiratory motion is stable, and becomes small in a region with large change in the respiratory motion. The graph (histogram) of FIG. 6B is changed by the continuous measurement and the count of the navigator echoes over a plurality of cycles, and a respiratory displacement having the maximum score is eventually selected as a displacement position (reference displacement) in a period in which the respiratory displacement is stable. In the example illustrated in FIG. 6B, the region 61 has the most highest score, and the region 61 is set as a reference displacement. A minimum value 601 of the displacement in this region is set as a reference position. Simultaneously, the width of the region when the score has been counted is set as a reference (reference displacement width) of the stability. For example, when the displacement in the regions 61 to 67 corresponds to 5 mm, the reference of the stability is also 5 mm.

Although the abovementioned determination of a reference displacement can be automatically performed, for example, the displacement detected from the navigator echo may be displayed on a display 410 as a form of the graph illustrated in FIG. 6A, a user may designate a period and the width of the region to be used in the main measurement on the graph, and the reference position/reference displacement width determination section 220 may receive the designation, and determine a displacement (reference displacement) in the stable period. The graph indicating a change in cyclic movement can be a change in a specific site to be displayed as a graph, for example, by displaying pixels of projection data acquired from the navigator echo as an image as they are.

Figure 7:
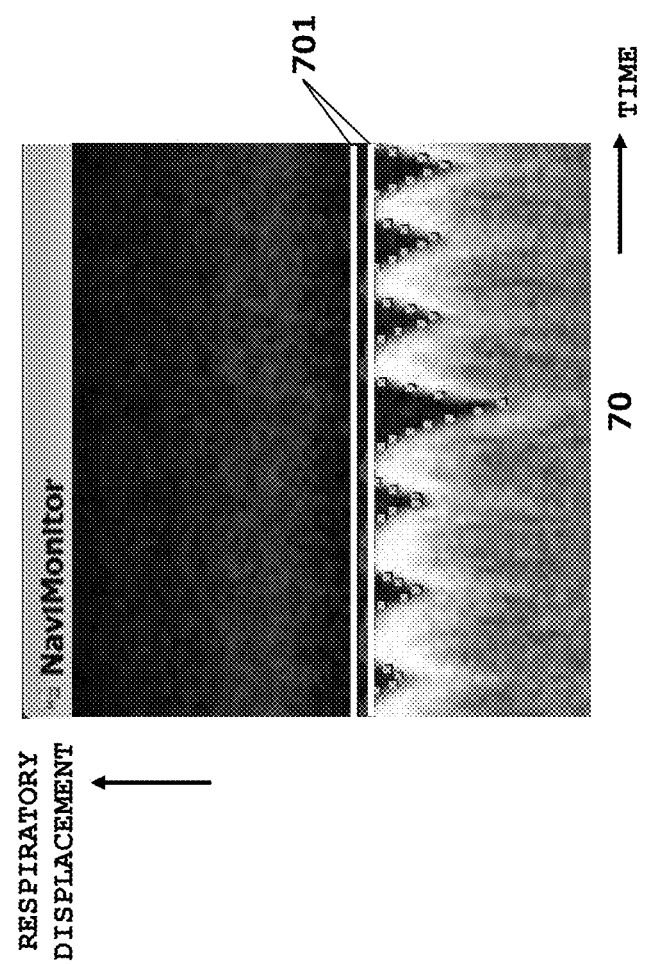
FIG. 7 is a diagram illustrating one example of a display screen of the respiratory displacement and a GUI.

FIG. 7 illustrates one example of a user interface on which a waveform is displayed. The reference is displayed as a double line 701 in a window 70 in which respiratory displacements are displayed in a time-series manner. The user can arbitrarily designate the reference of the displacement by changing a position of the line 701 with a drag of a mouse, an input with a key board, or the like. In addition, by changing an interval of the double line similarly, the reference of the stability can also be arbitrarily designated. Such a waveform or graph and the histogram in FIG. 6B may be monitored and held all the times during the imaging, and may be displayed on the display if necessary or all the times. Such a waveform display screen is displayed on the user interface to allow a progression state of the imaging to be grasped, and a shift of the displacement due to unexpected body motion to be known.

[Determination of Reference: S103, S104]

The navigation measurement is continued (S103) after the reference position/reference displacement width has been determined, and information (position and displacement width) on the displacement to be acquired after the navigator echo measurement is given to the determination section 230. The displacement width herein is a difference of reference positions by the temporally adjacent navigation measurements.

The determination section 230 compares a reference position and a reference displacement width determined by the reference position/reference displacement width determination section 220 with a reference position and a reference displacement width detected by the navigation measurement (S104), and determines whether the detected position satisfies the reference. Specifically, the determination is made as to whether positions detected in the two navigation measurements are within the reference displacement (equal to or higher than the reference position and equal to or lower than the reference position+the reference displacement width when the reference position is the minimum value of the reference displacement) and the displacement width is within the reference displacement width. As a result of the determination, if the reference is satisfied, the determination section 230 sends an instruction to the measurement control section 210, and starts the main measurement (S105) by the measurement section 100. If the detected position satisfies the reference position but the displacement width between the navigator echoes does not satisfy the reference displacement width, it is assumed that the body motion displacement is not stable, and the main measurement is not started. If neither the detected position nor the displacement width satisfy the condition, the navigation measurement (S103) is continued, and the determination at the step S104 is performed for each time when a navigator echo is measured.

[Main Measurement and Navigation Measurement: S105 to S108]

In the imaging sequence (S105) in the main measurement, a prescribed pulse sequence is repeated while a phase encode being changed for each TR, and data necessary for the image reconstruction is collected. The entire data is collected in the measurements in a plurality of times in a divided manner, and data of the predetermined number, that is part of the entire data is collected in one measurement. Although the number of data to be collected in one measurement varies depending on a pulse sequence to be used in the main measurement, one measurement time is made to be a time less than a time allocated for imaging in one cycle of the respiratory motion (the length of the longest section in which the abovementioned displacement of the specific site is within the range determined in advance). For example, the number of data that allows one measurement to be repeated twice or a plurality of times in the longest section is employed. A user may select/designate the number of data to be acquired in one measurement, for example, as one measurement parameter set by the user.

The measurement control section 210 performs the navigation measurement each time when one measurement has ended (S106). The number of the navigator echoes to be measured in the navigation measurement that is inserted between the measurement and the measurement only needs to enable acquisition of information on a displacement width, and is set to two echoes when information on a position and a displacement width is obtained in the navigation measurement. Moreover, one navigator echo may be set when the last displacement acquired in the previous navigation measurement is used for calculation of a displacement width. In other words, when two echoes can be acquired, positions of the diaphragm when these navigator echoes are acquired, and a displacement width that is a difference of the displacements can be acquired.

The determination section 230 determines whether the position and the displacement width detected by the navigation measurement (S106) satisfy the references, sends an instruction to the measurement control section 210 if satisfy, and the measurement control section 210 stores data acquired in the immediately prior measurement, and continues the main measurement. On the other hand, if the determination section 230 has determined that the reference is not satisfied, in other words, the detected position is not within the reference displacement or the detected displacement width exceeds the reference displacement width (S107), it is determined that the respiratory displacement is deviated from the stable cycle, the main measurement is to be discontinued, and the navigation measurement is performed.

[Discard of Immediately Prior Data: S108, S109]

When having determined that the references are not satisfied in the determination of the position of the diaphragm and the displacement width, the determination section 230 determines whether data in the immediately prior measurement is discarded (S108). For example, in a case where the position and the displacement width have been detected from two navigator echoes acquired before and after one measurement, when the displacement width exceeds the reference displacement width, the position of the diaphragm changes by exceeding the reference displacement width during the acquisition of the two navigator echoes, in other words, during the measurement, so that data acquired in the measurement has a low reliability. Accordingly, measurement data is discarded in this case. On the other hand, in a case where two navigator echoes are acquired in one measurement and a position of the diaphragm and a displacement width are determined, when a position of the first navigator immediately after the main measurement is within the reference displacement but the displacement width exceeds the reference displacement width, data in the immediately prior main measurement can be considered to be data acquired in a period when the respiratory motion is stable, and the data is not discarded. Moreover, in a case where data in the immediately prior measurement has already been discarded, it is determined that the discard of data is unnecessary. If it has been determined that the discard of data is unnecessary, the processing returns to the navigation measurement. Note that, although illustration is omitted in the flow in FIG. 5, in a case where it has been determined that the discard of data is unnecessary, when the measurement of the scheduled number of times is ended, the measurement is ended. Moreover, the determination processing S108 is omitted, and if it has been determined that the references are not satisfied in the determination of the position of the diaphragm and the displacement width, immediately prior data may be discarded all the times.

If the determination section 230 has determined as to be "discard of data", the measurement section 100 discards data in the immediately prior measurement (S109). Accordingly, the measurement control section 210 returns the counter to one before (set as "n=n−1"), and the measurement section 100 performs the navigation measurement (S106).

[Continuation and End of Main Measurement: S110]

If the main measurement is to be discontinued and the navigation measurement (S107) is started, the navigation measurement is continued until the position and the displacement width having been detected satisfy the references. If the reference is satisfied and the measurement of the scheduled number of times has been ended, the imaging is ended. If the measurement of the scheduled number of times has not been ended, the measurement control section 210 increments the counter, and starts a next measurement.

Figure 8:
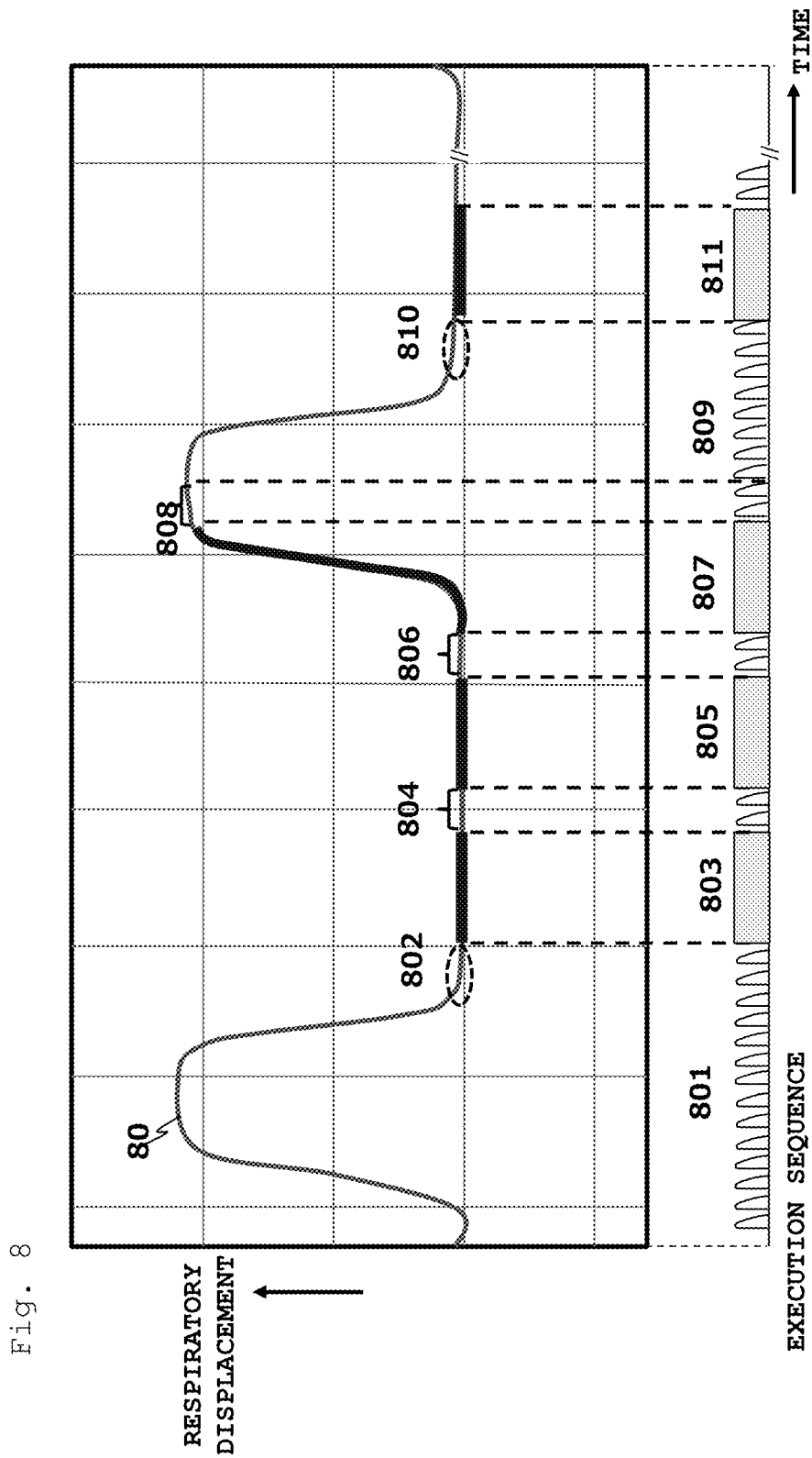
FIG. 8 is a diagram illustrating a specific example of imaging according to the first embodiment.

FIG. 8 illustrates a specific example of imaging according to the present embodiment. FIG. 8 is a diagram illustrating a relation between a respiratory displacement and an execution sequence. As illustrated, a navigation measurement 801 is executed immediately prior to the time when a respiratory displacement 80 enters a stable cycle, and a first measurement 803 executed at a time point 802 when the reference has been satisfied. A navigation measurement is performed after the first measurement has ended, and a determination 804 as to whether the reference is satisfied is made. In this example, two navigator echoes are measured in the navigation measurement, a determination as to whether positions obtained from these navigator echoes are within the reference displacement and a difference between these positions is within the reference displacement width is made, and a second measurement 805 is executed because the reference is satisfied. At an end time point of the second measurement, a navigation measurement and a determination 806 are similarly performed, and a third measurement 807 is executed. At an end time point of the third measurement, a navigation measurement and a determination 808 are similarly performed, however, the reference position herein is deviated from the reference displacement, so that the immediately prior measurement, in other words, data on the third measurement 807 is discarded. A navigation measurement 809 is continued without a fourth measurement being performed. The navigation measurement is continuously performed and the respiratory displacement is monitored, and when a determination (810) is made that the respiratory displacement again satisfies the reference, a main measurement (811) is started. The same applies hereinafter.

As has been explained in the foregoing, with the present embodiment, it is possible to insert a short-time navigation measurement between the measurement and the measurement, determine the continuation and the discontinuation for each measurement, and obtain, in a case of the discontinuation, by discarding data in the immediately prior measurement, an image with a high reliability from which an influence by the body motion has been eliminated, while ensuring the utmost time for the main measurement.

Moreover, with the present embodiment, a waveform of the displacement acquired in the navigation measurement is being displayed on the user interface 350 to allow a progression status of the imaging and a state of the displacement to be checked. Moreover, it is possible to set/change a measurement parameter, and set or change the reference position and the reference displacement width, via the user interface 350.

First Modification Example of First Embodiment

In the first embodiment, although the navigation measurement is necessarily performed between the measurement and the measurement, it is also possible to omit a part of the navigation measurement between the measurements using information on a stable period acquired in advance.

In other words, in the present modification example, when the measurement is performed in one cycle or more at the beginning of the imaging, a relation between the respiratory displacement and the time is stored in a one cycle or more, a stable cycle 405 (FIG. 4) is predicted based on the relation, thereby reducing the number of navigation measurements performed between the measurement and the measurement as small as possible. With reference again to FIG. 4 and FIG. 8, the present modification example will be described.

As illustrated in FIG. 4, from the relation between the respiratory displacement and the time acquired in advance, a time (period of 404) from a timing 401 when the respiratory displacement has been monitored to a timing 402 when the stable cycle 405 is started next time can be estimated. Moreover, a time (length of the stable period) until the stable cycle 405 is ended can also be estimated. Therefore, after it has been determined that the main measurement can be started as a result of the determination made at the timing (time point) 802 in FIG. 8, the main measurement is continuously performed to the time when the stable cycle is estimated to be ended, the navigation measurement is performed at the time point when the time has elapsed, and a determination is made as to whether the displacement at the time point satisfies the reference.

If the determination result at this time point is the same as the determination 806 in FIG. 8, for example, data on the immediately prior measurement 805 is stored, and the main measurement is continued. If the determination result is the same as the determination 808 in FIG. 8, data on the immediately prior measurement 807 is discarded, the navigation measurement is continued, and the displacement is monitored.

Note that, at the determination 806, even if the displacement satisfies the reference displacement, the movement direction of the displacement (in other words, whether the displacement width is plus or minus) can be reversed at the timing. In such a case, by comparing displacements monitored by two or more navigator echoes with each other, it is possible to determine the direction of displacement.

With the present modification example, it is possible to omit a part of the navigation measurements performed in the stable period in the first embodiment, in the example of FIG. 8, the determinations 804 and 806 and the navigation measurements therefor, or all of the navigation measurements, and improve the image data acquisition efficiency to the utmost.

Second Modification Example of First Embodiment

In the first embodiment, although the explanation has been made to the case where a displacement in one direction is detected by a navigator echo, displacements in a plurality of directions are detected in the present modification example.

For example, displacements of an abdominal wall of the subject with the respiration also occur in a front-back direction and a transverse direction (direction orthogonal to the body axis and front-back direction). With the occurrence of the displacements, there is a possibility that a position of an organ to be imaged may two-dimensionally change. In the present modification example, a two-dimensional displacement is monitored using a navigator echo that can detect displacements in a plurality of directions.

Methods of detecting displacements in a plurality of directions include a method in which two or more navigator echoes with different directions of navigation regions are used, and a method in which a phase encode is used in the navigation measurement, thereby obtaining information in a two-dimensional direction. In the former method, a displacement in the X-direction and a displacement in the Y-direction can be acquired, so that it is possible to monitor a two-dimensional displacement by synthesizing those displacements. Moreover, in the latter method, a low resolution image in which the phase encode is about 16 steps, for example, is obtained. By tracing a specific site of this image, for example, a prescribed position of an abdominal wall, it is possible to obtain a two-dimensional displacement.

With the present modification example, it is possible to eliminate body motion artifact with higher accuracy, by using navigator echoes in a plurality of directions.

Note that, the first and second modification examples in the first embodiment having been explained in the foregoing can be applied not only to the first embodiment but also to respective embodiments, which will be described below, as appropriate.

Second Embodiment

Although the first embodiment is based on the premise that the respiratory displacement of the subject does not shift during a series of the measurements, in other words, the reference position does not shift, the present embodiment is characterized in that control corresponding to a shift of the respiratory displacement that occurs during the imaging is performed.

Figure 9:
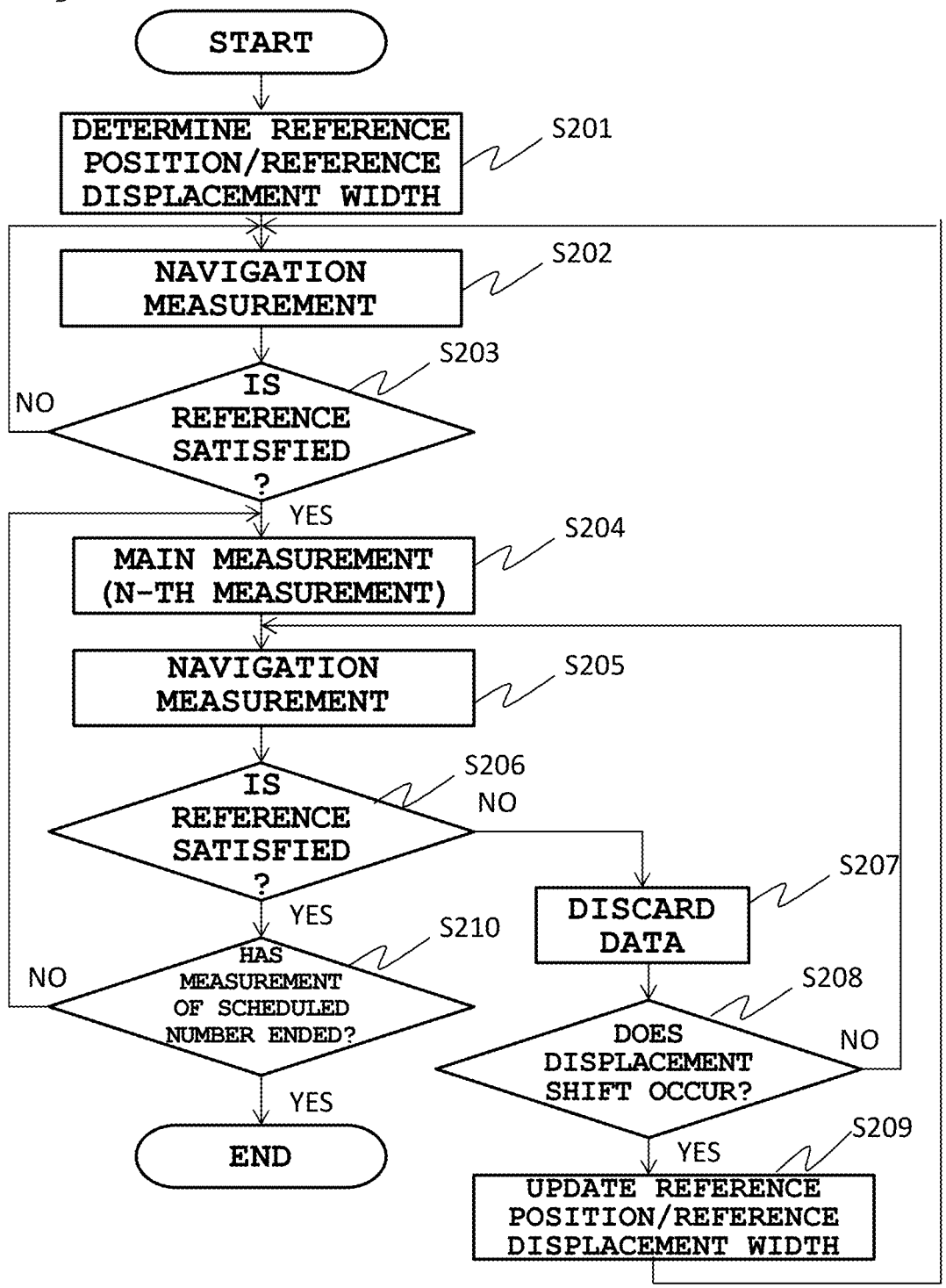
FIG. 9 is a flowchart illustrating an imaging procedure by an MRI device in a second embodiment.
Figure 10:
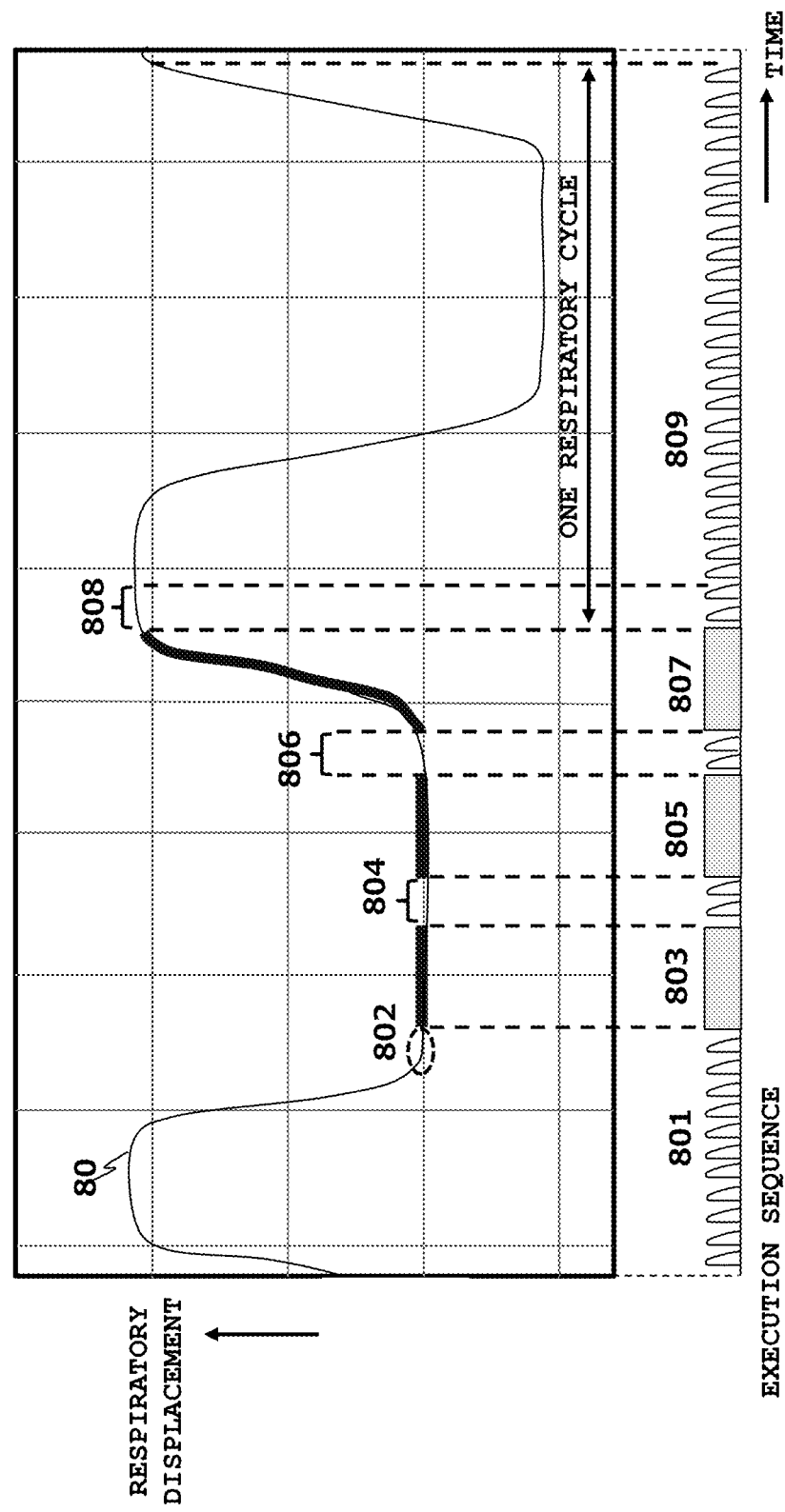
FIG. 10 is a diagram illustrating a specific example of imaging according to the second embodiment.

As processing in the present embodiment, different points from the first embodiment will be mainly described with reference to FIG. 9 and FIG. 10. Note that, in FIG. 10, the same reference numerals are given to the same elements as those in FIG. 8, and explanations thereof are omitted.

Also in the present embodiment, the following steps are similar to those in the first embodiment: after the inspection has been started, a navigation measurement is performed in a prescribed time, and a reference position and a displacement width are determined (S201); the navigation measurement is continuously performed until the reference is satisfied (S202); and if it has been determined that the reference is satisfied (S202), a measurement for acquiring image data and determination processing using a navigator echo between the respective measurements are performed (S204 to S206).

Figure 11:
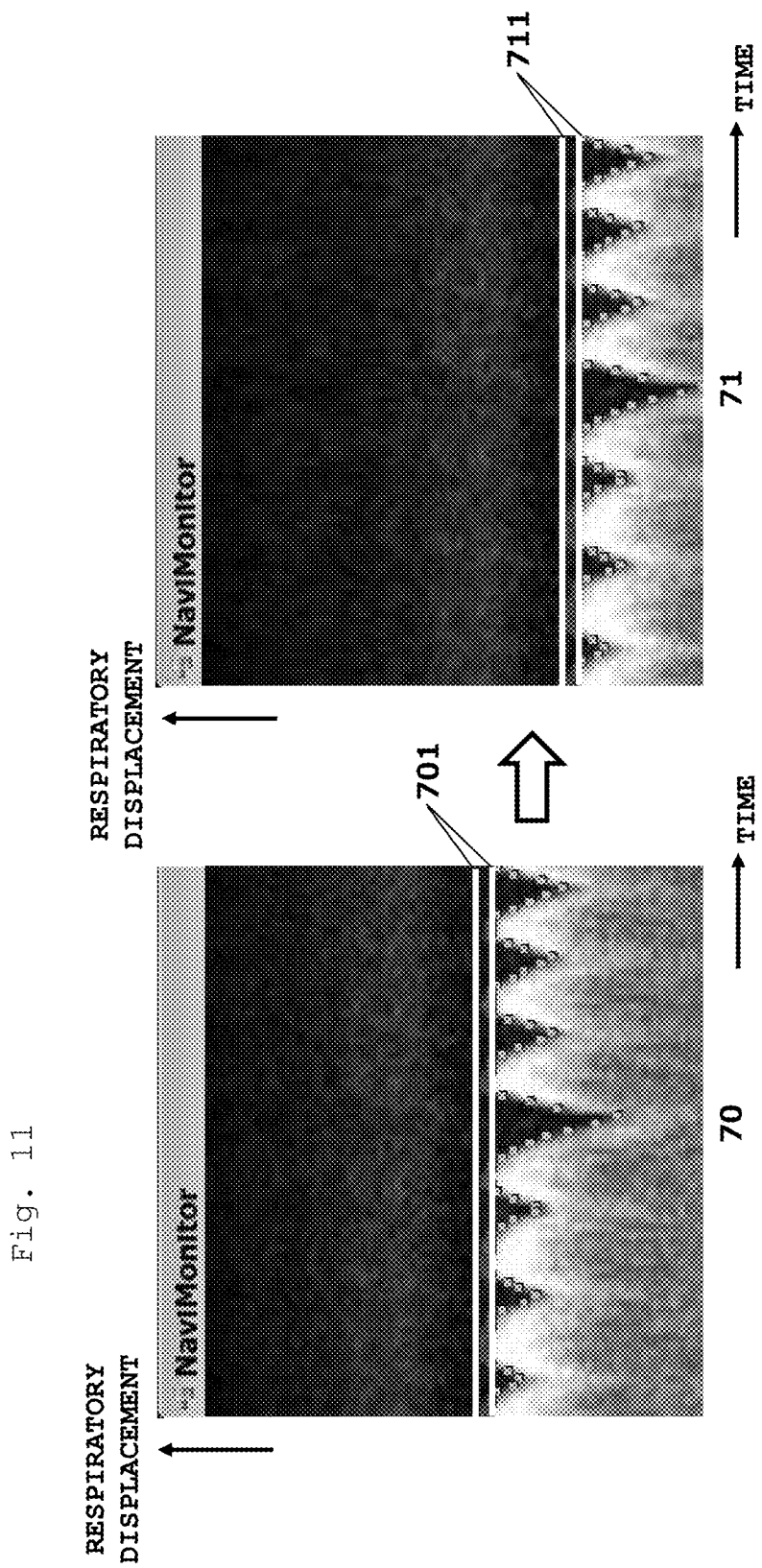
FIG. 11 is a diagram illustrating an example of GUIs for an update of a reference position.

In the present embodiment, if it has been determined that the reference is not satisfied at the determination processing (S206), immediately prior measurement data is discarded if necessary, the navigation measurement is continued, and a determination is made as to whether a shift has occurred (S208). Specifically, as illustrated in FIG. 10, during the navigation measurement 809, in a fixed period, for example, one respiratory cycle or more, no reference is satisfied, it is determined that a shift has occurred, and a reference position is again determined using a navigator echo (S209). The determination method of a reference position is similar to that in the first embodiment, the navigation measurement 809 in one respiratory cycle or more is performed, and the display 351 is caused to display the graph in FIG. 6A and the histogram in FIG. 6B thereon. The respiratory displacement is divided into a plurality of regions, a region with a high score of the navigator echo in each region is set as a reference displacement, and a position of the region (lower limit value) is determined as a reference position. As for the reference displacement width, a displacement width set at the beginning is used, but can be newly set. These determinations can be made with the user interface 350. FIG. 11 illustrates one example of a GUI for a reference update. When a state illustrated in the window 70 in which the respiratory displacement is displayed in a time-series manner is shifted to a state in a window 71, a user changes the reference displayed in the window as a double line from a position 701 to a position 711. The change is made with the input device 352 by a drag of a mouse, an input with a key board, or the like.

The reference position/reference displacement width determination section 220 updates the previous reference position to a newly determined reference position. Note that, although FIG. 10 illustrates the example in which the respiratory displacement shifts to the lower side, even in a case where the respiratory displacement shifts to the upper side, the reference is not satisfied (the reference displacement is not reached) in one respiratory cycle or more, and the same applies to the case.

When the update of the reference has been completed in this manner, the determination processing (S206) and the image data acquisition (S204, S206) are repeated until the collection of the entire image data is completed using the new reference.

As is in the foregoing, with the present embodiment, by updating the reference as appropriate, it is possible to perform the measurement in which the stable period of the respiratory motion is used at the utmost even when a respiratory shift of the displacement occurs. Moreover, both of the reference position and the reference displacement width are used in order to determine whether the reference is satisfied, whereby it is possible to fix a shift even if the reference displacement shifts in any direction.

First Modification Example of Second Embodiment

The present modification example is similar to the second embodiment in that the determination section 230 determines whether a shirt occurs in the respiratory displacement, and is characterized in that in the present modification example, a shift amount of the respiratory displacement is obtained, and in the imaging that is executed after the shift has occurred in the acquired data, an imaging slice position is shifted in accordance with the amount of shift of the respiratory displacement.

Figure 12:
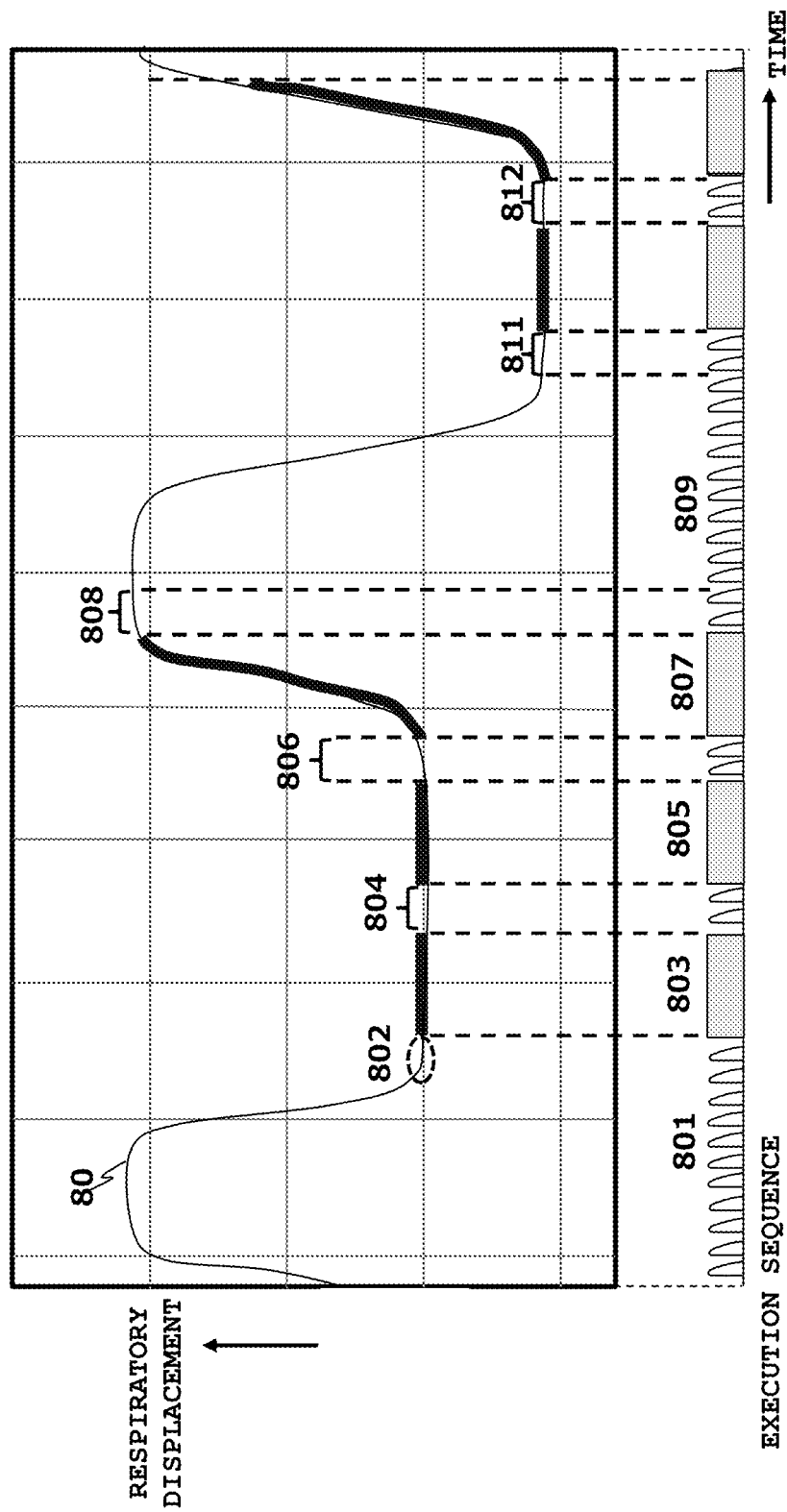
FIG. 12 is a diagram for explaining a first modification example in the second embodiment.

Therefore, in the present modification example, as illustrated in FIG. 12, when the navigation measurement is continuously executed after the measurement in the stable period, if it has been determined at a determination 812 that only the stability (only the reference displacement width) satisfies the reference, a respiratory displacement in the determination 812 is compared with the reference displacement used for the determination in the previous determinations 804, 806, and the like, a difference thereof is used as a shift amount, and a slice position in the imaging after the shift is shifted in accordance with the shift amount. The shift of the slice position can be adjusted, for example, by controlling the RF transmitter 110 in the main measurement to change the center frequency of an excitation RF pulse. Alternatively, the offset amount of the slice gradient magnetic field to be applied with the RF pulse may be changed.

An irradiation frequency change in accordance with the amount of shift can be calculated as follows. In a case where the magnetic field center is used as a reference position, an irradiation frequency F(Z) at a certain slice position Z is given by an expression (1) from a center frequency F0, a magnetic rotation ratio γ, a slice selection gradient magnetic field Gs, and a position Z. By using the expression (1), F(Z) in accordance with the shift amount Z measured from the navigator echo is calculated, and is reflected on an imaging sequence.

$$F(Z)=F0+\gamma \times (Gs \times Z) \quad (1)$$

When an offset is present in the reference position, F0 in the expression (1) may be replaced with a value (frequency F1 including the offset) different from the center frequency.

Moreover, when a shift has occurred, the horizontal axis of the histogram (histogram indicating a relation between the displacement and the echo score) such as that illustrated in FIG. 6B also changes, so that in the determination 812 and the like after the shift, a determination as to whether the reference is satisfied is made by using the displacement having a maximum score in the histogram as a reference displacement.

In the second embodiment, when a shift has occurred in the respiratory displacement, data needs to be acquired in one respiratory cycle or more in order to update the reference position and the reference displacement width, and when a user sets a reference position, the processing time for the setting is necessary. However, with the present modification example, a time loss due to the acquisition of data for updating the reference does not occur, so that it is possible to acquire image data with higher efficiency.

Second Modification Example of Second Embodiment

The present modification example is characterized in that when the displacement shifts, a user can select a mode (second embodiment) in which the reference position and the reference displacement width are updated and the main measurement and the navigation measurement are continued or a mode (first modification example) in which when the displacement is shifted, a slice position of the main measurement is shifted.

Figure 13:
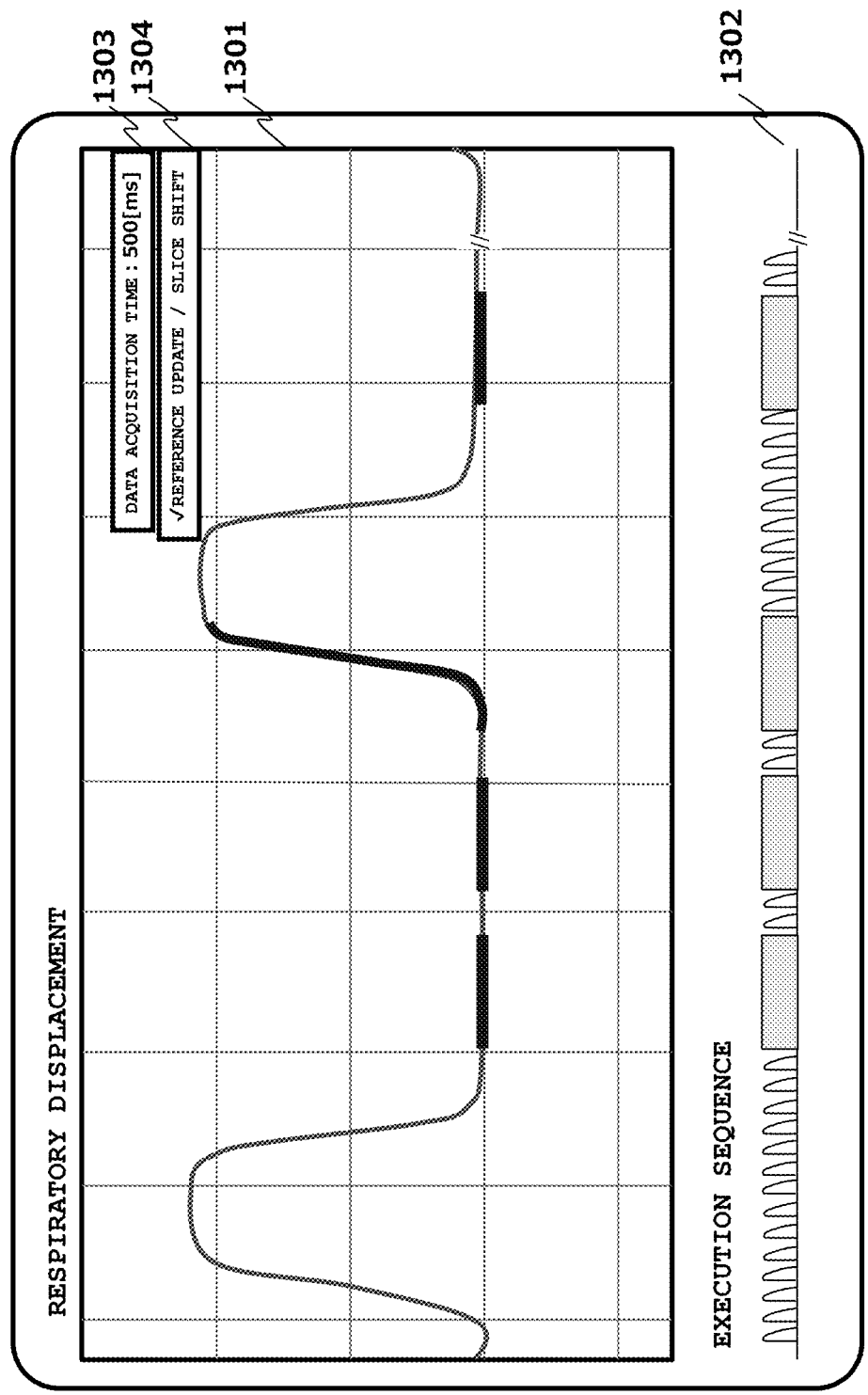
FIG. 13 is a diagram for explaining a second modification example in the second embodiment.

FIG. 13 illustrates a screen example that is presented to a user. In this screen example, a graph display section 1301 that indicates a respiratory displacement during the imaging, a processing display section 1302 that indicates a timing of an execution sequence, a time display section 1303 that displays a time of one measurement, in other words, a data acquisition period, and a mode selection section 1304 that receives a selection of the mode by a user, are provided. The mode selection section 1304 is configured to receive the selection of either one of a mode in which the reference is updated and a mode in which a slice position is shifted, and display which one has been selected with a check mark or a luminance change.

When a user desires, for example, to shorten the measurement time as short as possible, by having selected the slice shift mode, the user can perform smooth imaging without the necessity of changing the reference position each time a shift occurs. Moreover, when the reference position update mode is selected, it is possible to make the reference position determination with high accuracy, and thus to acquire an image with a better image quality.

With the present modification example, it is possible to give a user the flexibility of selection, and to perform imaging in which the user has selected the priority of the image quality or the measurement time.

Although the respective embodiments of the present invention have been explained in the foregoing, the respective embodiments and modification examples of the present invention can be combined to each other as appropriate unless causing the technical contradiction, and the addition and the omission of elements that are not indispensable are included in the present invention.

REFERENCE SIGNS LIST

40: respiratory displacement, 41 to 47: displacement region, 80: respiratory displacement, 100: measurement section, 102: magnet, 103: gradient magnetic field coil, 104: high frequency coil (RF coil), 105: RF probe, 106: transmitter, 109: gradient magnetic field power supply, 110: RF detector, 200: control section, 210: measurement control section, 220: reference position/reference displacement width determination section, 230: determination section, 300: signal processor, 310: image reconstruction section, 320: image processor, 350: user interface, 351: display, 352: input device, 405: stable period

The invention claimed is:

1. A magnetic resonance imaging device comprising:
a measurement processor that executes a navigation measurement to acquire a navigator echo that specifies a cyclic displacement of an object to be inspected, and a main measurement to acquire an image of the object to be inspected; and
a control processor that controls an operation of the measurement processor such that after having performed the navigation measurement over at least one cycle of the cyclic displacement, the measurement processor repeats the main measurement in a predetermined unit, and performs the navigation measurement to acquire one or a plurality of the navigator echoes between the repeated main measurements in at least two temporally adjacent predetermined units, wherein the control processor includes a determination processor that determines, by using the navigator echo acquired over the at least one cycle of the cyclic displacement in the navigation measurement, a reference position and a reference displacement width in the cyclic displacement that has a maximum navigator echo score obtained from a plurality of divided displacement regions of the cyclic displacement, and determines, by using a navigator echo acquired immediately after the measurement in the predetermined unit, and the reference position and the reference displacement width, whether to continue or discontinue the main measurement in the predetermined unit, the measurement processor repeats the main measurement in the predetermined unit when the determination processor has determined to continue the main measurement in the predetermined unit, and performs the navigation measurement when the determination processor has determined to discontinue the main measurement in the predetermined unit, and the measurement processor acquires two navigator echoes in the navigation measurement between the main measurements in the predetermined units, and the determination processor determines, by using displacement positions detected from these navigator echoes and a difference between the determined positions, whether to continue or discontinue the main measurement in the predetermined unit, wherein the main measurement is continued, if both the displacement positions and the difference between the determined positions are within the reference displacement width wherein the reference position is set as having a minimum value of the reference displacement, or otherwise the main measurement is discontinued and the preceding main measurement is discarded.

2. The magnetic resonance imaging device according to claim 1, characterized in that the measurement processor discards data acquired in a measurement in an immediately prior predetermined unit when the determination processor has determined to discontinue the measurement in the predetermined unit.

3. The magnetic resonance imaging device according to claim 1, characterized in that the measurement processor acquires at least two navigator echoes in the navigation measurement between the main measurements in the at least two temporally adjacent predetermined units, the determination processor detects a displacement and a displacement width from the two navigator echoes, compares the displacement and the displacement width thus detected with the reference position and the reference displacement width, and determines whether to continue or discontinue the main measurement in the predetermined unit.

4. The magnetic resonance imaging device according to claim 1, characterized in that the measurement processor performs the navigation measurement over one cycle of the cyclic displacement when the determination processor has determined to discontinue the main measurement in the predetermined unit, and the determination processor determines, by using a navigator echo acquired in the latest navigation measurement over one cycle of the cyclic displacement, a reference position and a reference displacement width in the cyclic displacement, and updates a reference position and a reference displacement width having been determined before.

5. The magnetic resonance imaging device according to claim 1, characterized in that the measurement processor changes, when the determination processor has determined that only the detected displacement width satisfies the reference displacement width, by using a shift amount of the cyclic displacement calculated by using a position detected from the navigator echo having been used for a current determination and the reference position having been used for a prior determination, wherein the reference position is a condition of the main measurement.

6. The magnetic resonance imaging device according to claim 1, characterized in that the measurement processor acquires displacements in two or more directions in the navigation measurement.

7. The magnetic resonance imaging device according to claim 1, characterized in that the control processor further includes a display controller that causes a display device to display the displacement of the object to be inspected specified by the navigation measurement.

8. The magnetic resonance imaging device according to claim 7, characterized by further including an interface processor that receives designation of a reference position and a reference displacement width by a user using the displacement of the object to be inspected displayed on the display device.

9. The magnetic resonance imaging device according to claim 1, characterized in that the navigation measurement comprises a phase encode.

* * * * *